(12) United States Patent
Schaetzl

(10) Patent No.: US 9,486,599 B2
(45) Date of Patent: Nov. 8, 2016

(54) APPARATUS AND METHOD FOR CONTROLLED DELIVERY OF A BREATHING GAS TO THE RESPIRATORY TRACTS OF A USER

(75) Inventor: Stefan Schaetzl, Weilheim (DE)

(73) Assignee: ResMed R&D Germany GmbH (AU)

( * ) Notice: Subject to any disclaimer, the term of this patent is extended or adjusted under 35 U.S.C. 154(b) by 370 days.

(21) Appl. No.: 12/736,692

(22) PCT Filed: Apr. 6, 2009

(86) PCT No.: PCT/EP2009/002532
§ 371 (c)(1),
(2), (4) Date: Nov. 1, 2010

(87) PCT Pub. No.: WO2009/132753
PCT Pub. Date: Nov. 5, 2009

(65) Prior Publication Data
US 2011/0108033 A1    May 12, 2011

(30) Foreign Application Priority Data

Apr. 30, 2008  (EP) .................... 08008301

(51) Int. Cl.
A61M 15/08  (2006.01)
A61M 16/00  (2006.01)
A61M 15/00  (2006.01)
A61M 16/06  (2006.01)

(52) U.S. Cl.
CPC ................ *A61M 16/0666* (2013.01)

(58) Field of Classification Search
None
See application file for complete search history.

(56) References Cited

U.S. PATENT DOCUMENTS

| | | | |
|---|---|---|---|
| 3,638,926 A | 2/1972 | Melville et al. | |
| 3,786,809 A | 1/1974 | Kitrilakis | |
| 3,912,795 A | 10/1975 | Jackson | |
| 4,249,527 A | 2/1981 | Ko et al. | |
| 4,278,082 A | 7/1981 | Blackmer | |
| 4,281,651 A | 8/1981 | Cox | |
| 4,369,777 A | 1/1983 | Lwoff et al. | |
| 4,511,355 A * | 4/1985 | Franetzki et al. | 604/131 |
| 4,637,384 A | 1/1987 | Schroeder | |
| 4,643,183 A | 2/1987 | Seilinger | |
| 4,782,832 A | 11/1988 | Trimble et al. | |

(Continued)

FOREIGN PATENT DOCUMENTS

| | | |
|---|---|---|
| DE | 2406679 A1 | 8/1975 |
| EP | 0885623 B1 | 11/2004 |

(Continued)

OTHER PUBLICATIONS

Office Action for corresponding European Application No. 08008301.7, mailed Oct. 13, 2011, 4 pages.

(Continued)

*Primary Examiner* — Bradley Philips
*Assistant Examiner* — Eric Bryant
(74) *Attorney, Agent, or Firm* — Lerner, David, Littenberg, Krumholz & Mentlik, LLP

(57) ABSTRACT

An apparatus for controlled delivery of a flow of breathing gas to the respiratory tracts of a user includes a blower unit adapted to provide a gas flow, a nasal cannula with first and second outlets, and first and second gas paths connecting the blower unit to the first and second outlets, respectively. The Characteristics of the gas flow through each outlet can be controlled, sensed and/or adjusted independently.

34 Claims, 1 Drawing Sheet

(56) References Cited

U.S. PATENT DOCUMENTS

| | | | |
|---|---|---|---|
| 4,944,310 A | 7/1990 | Sullivan | |
| 4,967,744 A * | 11/1990 | Chua | 128/204.18 |
| 4,989,599 A | 2/1991 | Carter | |
| 5,031,612 A | 7/1991 | Clementi | |
| 5,065,756 A | 11/1991 | Rapoport | |
| 5,245,995 A | 9/1993 | Sullivan et al. | |
| 5,349,946 A | 9/1994 | McComb | |
| 5,392,770 A * | 2/1995 | Clawson et al. | 128/203.27 |
| 5,490,502 A | 2/1996 | Rapoport et al. | |
| 5,537,997 A | 7/1996 | Mechlenburg et al. | |
| 5,682,881 A | 11/1997 | Winthrop et al. | |
| 5,692,497 A | 12/1997 | Schnitzer et al. | |
| 5,704,345 A | 1/1998 | Berthon-Jones | |
| 6,024,088 A * | 2/2000 | Ishikawa et al. | 128/204.21 |
| 6,240,921 B1 | 6/2001 | Brydon et al. | |
| 6,325,063 B1 | 12/2001 | Volgyesi | |
| 6,345,538 B1 * | 2/2002 | Krahbichler et al. | 73/861.27 |
| 6,349,724 B1 | 2/2002 | Burton et al. | |
| 6,363,933 B1 | 4/2002 | Berthon-Jones | |
| 6,367,472 B1 | 4/2002 | Koch | |
| 6,398,739 B1 | 6/2002 | Sullivan et al. | |
| 6,467,477 B1 | 10/2002 | Frank et al. | |
| 6,516,801 B2 | 2/2003 | Boussignac | |
| 6,523,538 B1 * | 2/2003 | Wikefeldt | 128/204.18 |
| 6,629,527 B1 | 10/2003 | Estes et al. | |
| 6,635,021 B1 | 10/2003 | Sullivan et al. | |
| 6,672,300 B1 * | 1/2004 | Grant | 128/204.26 |
| 6,770,037 B2 | 8/2004 | Sullivan et al. | |
| 6,776,163 B2 | 8/2004 | Dougill et al. | |
| 6,994,089 B2 | 2/2006 | Wood | |
| 7,004,908 B2 | 2/2006 | Sullivan et al. | |
| 7,080,645 B2 | 7/2006 | Genger et al. | |
| 7,141,021 B2 | 11/2006 | Sullivan et al. | |
| 7,314,046 B2 | 1/2008 | Schroeder et al. | |
| 8,171,935 B2 | 5/2012 | Cortez, Jr. et al. | |
| 8,220,458 B2 | 7/2012 | Landis et al. | |
| 8,220,463 B2 | 7/2012 | White et al. | |
| 8,225,796 B2 | 7/2012 | Davenport et al. | |
| 8,333,195 B2 | 12/2012 | Cortez, Jr. et al. | |
| 8,490,621 B2 | 7/2013 | Radomski et al. | |
| 2002/0096173 A1 * | 7/2002 | Berthon-Jones et al. | 128/204.23 |
| 2003/0181917 A1 | 9/2003 | Gertner | |
| 2003/0209246 A1 | 11/2003 | Schroeder et al. | |
| 2004/0016430 A1 | 1/2004 | Makinson et al. | |
| 2004/0173210 A1 | 9/2004 | Campbell | |
| 2004/0182386 A1 | 9/2004 | Meier | |
| 2004/0261797 A1 | 12/2004 | White et al. | |
| 2005/0011523 A1 | 1/2005 | Aylsworth et al. | |
| 2005/0121033 A1 | 6/2005 | Starr et al. | |
| 2005/0143617 A1 | 6/2005 | Auphan | |
| 2005/0178383 A1 * | 8/2005 | Mackie et al. | 128/203.16 |
| 2005/0284484 A1 * | 12/2005 | Curti | A61B 5/083; 128/207.18 |
| 2006/0000475 A1 | 1/2006 | Matthews et al. | |
| 2006/0169281 A1 * | 8/2006 | Aylsworth et al. | 128/204.23 |
| 2007/0107737 A1 * | 5/2007 | Landis et al. | 128/207.18 |
| 2007/0175473 A1 | 8/2007 | Lewis et al. | |
| 2007/0272240 A1 | 11/2007 | Aylsworth et al. | |
| 2008/0027344 A1 * | 1/2008 | Terry | 600/532 |
| 2008/0035202 A1 * | 2/2008 | Lee | G01F 25/0038; 137/10 |
| 2008/0041393 A1 | 2/2008 | Bracken | |
| 2008/0051674 A1 | 2/2008 | Davenport et al. | |
| 2009/0320851 A1 * | 12/2009 | Selvarajan | A61M 16/0683; 128/207.13 |
| 2010/0192957 A1 | 8/2010 | Hobson et al. | |
| 2011/0108033 A1 | 5/2011 | Schaetzl | |
| 2011/0125052 A1 | 5/2011 | Davenport et al. | |
| 2011/0253136 A1 * | 10/2011 | Sweeney | A61M 16/16; 128/203.12 |
| 2012/0017904 A1 | 1/2012 | Ratto et al. | |
| 2012/0125332 A1 | 5/2012 | Niland et al. | |

FOREIGN PATENT DOCUMENTS

| | | |
|---|---|---|
| EP | 2113274 A1 | 11/2009 |
| WO | 0141854 A2 | 6/2001 |
| WO | 03066145 A1 | 8/2003 |
| WO | 2004020031 A1 | 3/2004 |
| WO | 2005079726 A1 | 9/2005 |
| WO | 2006096450 A2 | 9/2006 |
| WO | 2006126900 A1 | 11/2006 |
| WO | 2007033347 A2 | 3/2007 |
| WO | 2007045017 A2 | 4/2007 |
| WO | 2007064750 A2 | 6/2007 |
| WO | 2007103715 A2 | 9/2007 |
| WO | 2007/140478 | 12/2007 |
| WO | 2007143535 A2 | 12/2007 |
| WO | 2008030592 A2 | 3/2008 |
| WO | 2008060295 A2 | 5/2008 |
| WO | 2008076230 A2 | 6/2008 |
| WO | 2008091164 A1 | 7/2008 |
| WO | 2008096307 A1 | 8/2008 |
| WO | 2009064202 A2 | 5/2009 |
| WO | 2009124198 A2 | 10/2009 |
| WO | 2009132753 A1 | 11/2009 |
| WO | 2009146484 A1 | 12/2009 |
| WO | 2010014824 A2 | 2/2010 |
| WO | 2011068418 A1 | 6/2011 |
| WO | 2011078703 A1 | 6/2011 |
| WO | 2011149362 A1 | 12/2011 |
| WO | 2012053910 A1 | 4/2012 |
| WO | 2012164407 A1 | 12/2012 |
| WO | 2013148754 A1 | 10/2013 |
| WO | 2013151447 A1 | 10/2013 |
| WO | 2013172722 A1 | 11/2013 |
| WO | 2013176557 A1 | 11/2013 |
| WO | 2013187776 A1 | 12/2013 |
| WO | 2014031010 A1 | 2/2014 |
| WO | 2014035261 A1 | 3/2014 |
| WO | 2014095736 A1 | 6/2014 |
| WO | 2014142681 A1 | 9/2014 |
| WO | 2014142682 A1 | 9/2014 |
| WO | 2014182179 A2 | 11/2014 |
| WO | 2014196875 A1 | 12/2014 |
| WO | 2015020540 A1 | 2/2015 |
| WO | 2015033288 A1 | 3/2015 |

OTHER PUBLICATIONS

International Search Report for PCT/EP2009/002532 mailed Jul. 13, 2009.

International Search Report, PCT/AU09/00671, dated Sep. 9, 2009.

McGinley, Brian, M., et al., A Nasal Cannula can be Used to Treat Obstructive Sleep Apnea, Am J Respir Crit Care Med, vol. 176, pp. 194-200, 2007.

Sreenan, MB, Con, et al., High-Flow Nasal Cannulae in the Management of Apnea of Prematurity: A Comparison with Conventional Nasal Continuous Positive Airway Pressure, Pediatrics, vol. 107, No. 5, May 2001.

U.S. Appl. No. 61/058,659, filed Jun. 4, 2008.

Statement of Case in the Matter of Patents Act 1953 and In the Matter of New Zealand Patent Application No. 589990 in the name of ResMed Limited and In the Matter of an Opposition thereto by Fisher & Paykel Healthcare Limited under Section 21, Dated Oct. 22, 2013.

Patents Form No. 15, "First Amended Notice of Opposition to Grant of Patent (Section 21)", Oct. 22, 2013.

Exhibit ST01—Statutory Declaration of Stainslav Tatkov, In the Matter of Patents Act 1953 and In the Matter of New Zealand Patent Application No. 589990 in the name of ResMed Limited and In the Matter of an Opposition thereto by Fisher & Paykel Healthcare Limited under Section 21, Dated Nov. 24, 2014.

Counterstatement in the Matter of Patents Act 1953 and In the Matter of New Zealand Patent Application No. 589990 in the name of ResMed Limited (The Applicant) and In the Matter of an Opposition thereto by Fisher & Paykel Healthcare Limited (The Opponent), Dec. 20, 2013.

(56) References Cited

OTHER PUBLICATIONS

First Amended Statement of Case, In the Matter of Patents Act 1953 and In the Matter of New Zealand Patent Application No. 589990 in the name of ResMed Limited and In the Matter of an Opposition thereto by Fisher & Paykel Healthcare Limited under Section 21, Nov. 25, 2014.

Exhibit PP001—Evidence of Prior Publication in New Zealand regarding D1-D8, In the Matter of Patents Act 1953 and In the Matter of New Zealand Patent Application No. 589990 in the name of ResMed Limited and In the Matter of an Opposition thereto by Fisher & Paykel Healthcare Limited under Section 21, Nov. 24, 2014.

Supplementary Partial European Search Report for Application No. EP09756949.5 dated Aug. 12, 2015.

Extended European Search Report for application No. EP16167102 dated Aug. 18, 2016.

* cited by examiner

APPARATUS AND METHOD FOR CONTROLLED DELIVERY OF A BREATHING GAS TO THE RESPIRATORY TRACTS OF A USER

This application is the U.S. national phase of International Application No. PCT/EP2009/002532 filed 6 Apr. 2009, which designated the U.S., and claims priority to European application No. 08008301.7, filed 30 Apr. 2008, the entire contents of each of which are hereby incorporated by reference.

FIELD OF THE INVENTION

The present invention is related to an apparatus for controlled delivery of a flow of breathing gas to the respiratory tracts of a user. The invention further relates to a method of controlling such an apparatus and to a method of delivering a flow of breathable gas to the respiratory tracts of a user via a nasal cannula with first and second outlets.

BACKGROUND OF THE INVENTION

Several such devices for delivering breathing gas to a patient are known in the art and widely used in the medical and therapeutical sectors. One important employment of the delivery of a breathing gas relates to treatment of sleep-related respiratory disorders, in particular of obstructive sleep apnea (OSA). Patients suffering from OSA are often supplied with a continuous positive airway pressure (CPAP) and/or a predetermined flow of a breathing gas during rest or sleep periods. This is achieved by the patient wearing a suitable breathing mask, which is connected to an apparatus, also referred to as blower, providing the necessary pressure and/or air flow. Due to the pressure being higher than ambient pressure the obstructed airways of the patient are "pushed" open, also referred to as pneumatic splinting, allowing for an adequate supply of breathing gas including oxygen.

In the art, there are known "closed" breathing masks which usually sealingly cover mouth and/or nose of a patient or user. Also known are "open" interfaces, such as a nasal cannula, which do not cover the mouth and/or nose of a patient but direct the breathing gas flow into the nose and/or mouth of a patient. Such cannula or "open" system is generally not sealed against the nose or mouth of a patient. Nasal cannulas are typically preferred by the user because they are more comfortable than "closed" masks, which usually are more bulky and have to be fixed to the user's head by a headband. Since these masks generally have to be applied over long periods, often during the whole night, there size and weight may turn out to influence the comfort of a patient.

However, such "open" interfaces and the systems known in the art applying such "open" interfaces have a number of disadvantages. These disadvantages particularly include the reduced operating conditions and the reduced application area vis-à-vis "closed" systems. In particular, it is problematic to adjust the applied therapy during therapy depending on the current patient conditions and particularly depending on the upper airway conditions of the user. This is particularly due to the "open" interface not being able to simultaneously perform therapy and diagnostic measures. It is also not possible to observe the severity of sleep disordered breathing during therapy. This would, however, be necessary to make sure that the necessary therapy is applied, e.g., that a patient is transferred to a standard CPAP therapy if he shows enhanced snoring or obstructive events.

SUMMARY OF THE INVENTION

It is therefore an object of the present invention to provide an improved device for controlled delivery of a flow of breathing gas to the respiratory tracts of a user, in particular a device with an "open" interface and preferably an "open" nasal cannula, which overcomes the above-mentioned problems and disadvantages. It is a further object of the present invention to provide an improved method of controlling such a device.

These and other objects are achieved by the features of the independent claims. The dependent claims relate to preferred embodiments.

The present invention is based on the idea to use a dual lumen cannula, wherein both lumens may be controlled independently. Thus, two gas (flow) paths or channels are provided, which either can provide an airflow to the nose of a user or act as a pressure sensing line. This allows for diagnosis while providing therapy at the same time. One of the two gas paths or channels can be used for diagnosis while the other gas path or channel is used for providing therapy, wherein the use of the channels may be changed. Also, both channels can perform the same use, such as, e.g., therapy or diagnosis. Alternatively, the channels may be used to perform simultaneously different kinds of therapy or diagnosis.

Each of the lumens or channels are provided with nasal prongs at one end thereof in order to be applied to a patients nose. Preferably, the two channels are distinct and separated channels. Each of the channels is in communication with one nasal prong or one nostril of the patient.

Accordingly, the present invention provides an apparatus for controlled delivery of a flow of breathing gas to the respiratory tracts of a user, said apparatus comprising a blower unit adapted to provide a gas flow, a nasal cannula with first and second outlets, and first and second flow paths connecting the blower unit to the first and second outlets, respectively, wherein characteristics of the gas flow through each outlet can be controlled, sensed and/or adjusted independently.

These characteristics of the gas flow preferably comprise a flow rate and/or a pressure of the provided gas flow. However, other characteristics or parameters of the gas flow may be controlled or adjusted as well, for example the humidity and/or temperature of the provided breathing gas. It is also preferred to adjust the composition of the breathing gas, e.g., the oxygen concentration thereof. The concentration of optional therapeutics may also be controlled or adjusted by the apparatus.

Nevertheless, according to a specifically preferred embodiment the characteristics and particularly the flow rate and/or pressure in both flow paths can be adjusted or controlled independently. A preferred solution allows for switching the flow rate of the breathing gas through one of the flow paths on and off. This may be done, e.g., providing a valve in the flow path and by controlling the state of said valve. A pressure sensor provided in the other flow path enables the apparatus to detect a dynamic pressure signal resulting from the respiratory cycle of a user. Accordingly, the apparatus according to the present invention is able to simultaneously provide therapy and to perform diagnosis via the two flow paths, e.g., by providing a flow of breathing gas through one of said flow paths and by sensing characteristics of the gas flow, such as a dynamic pressure signal, via the other flow path.

If the diagnosis channel is not needed continuously, the flow rate in the second flow path may be adjusted to the one in the first flow path intermittently. For example, the valve controlling the flow rate in the second flow path may be switched on and off in predetermined time intervals. This allows to perform, e.g., diagnosis at predefined times while enhancing the therapy by the use of two channels in between these diagnosis times or intervals.

According to a more preferred embodiment, both the first and second flow paths each comprise a valve and a pressure sensor. Thus, an air or breathing gas flow can be provided through one of the first and second flow paths while the other of the first and second flow paths is used for detection, wherein the function of the first and second flow paths can be interchanged periodically. This guarantees a more continuous and/or symmetric supply with breathing gas. The period of interchange may be adjusted to, e.g., the respiratory cycle of the user. For instance, during one respiratory cycle (inhalation and exhalation) the first flow path may be pressurized, while during the subsequent respiratory cycle the second flow path will be pressurized. Consequently, the second and first flow paths are used for diagnosis, respectively.

Of course, other therapy-diagnosis schemes are possible as well. It is in particular advantageous to activate diagnosis only intermittently and to provide therapy via both flow paths during the remaining time.

As already mentioned, other parameters may be controlled as well. It is particularly preferred that the apparatus according to the present invention further comprises a humidifier to adjust the humidity of the provided breathing gas to a predetermined value. Optionally, said value may be adjusted in response to the detected dynamic pressure signal. The humidifier may be any known humidifier, for instance a warm-water/warm-air humidifier.

Preferably, the apparatus further comprises diaphragm filters to protect the valve(s) from condensing water.

Provision is also made for a control unit for analyzing the detected dynamic pressure signal and/or for controlling, e.g., the blower unit, the state of the valves, the humidifier and the like. The control unit may comprise several sub-units, such as breathing detector, a trigger unit, a flow controller, a motor controller, and a supervisor unit to name but a few.

Preferably, the apparatus according to the present invention can be used as an open CPAP system, i.e. as a CPAP system, wherein the patient interface is not sealed against the patient's face. For example, the nasal cannula of the apparatus is preferably adapted not to seal with the user's nostrils.

The present invention is further directed to a method of controlling an apparatus for controlled delivery of a flow of breathing gas, in particular an apparatus as described above. The inventive method comprises activating a first gas flow in a first flow path; measuring a dynamic pressure signal in a second flow path; and optionally adjusting a parameter of the first gas flow in response to the measured signal.

Therein, the first gas flow may be activated, e.g., by opening a valve or by otherwise increasing a flow rate or pressure within the first flow path. The dynamic pressure signal is preferably measured with a pressure sensor, which is protected from condensing water by a diaphragm filter.

The breathing gas according to the present invention is preferably air. However, in some embodiments the oxygen concentration is higher than in air. Furthermore, an aerosol or other additive, e.g. therapeutics, may be added to the air. The air may be humidified and/or warmed.

It is preferred that activating the first gas flow and measuring the dynamic pressure signal are performed simultaneously. It is further preferred that the single steps of the method are performed repeatedly, wherein the functionality of the first and second gas paths are most preferably interchanged after each repetition or a number of repetitions.

The parameter of the first gas flow to be adjusted may be one or a combination of the following parameters: flow rate of the first gas flow, pressure within the first flow path, temperature and/or humidity of the first gas flow, oxygen concentration of the first gas flow, the concentration of any additives, e.g. therapeutics, the period of repetition.

The present invention further relates to a method of delivering a flow of breathable gas to the respiratory tracts of a user via a nasal cannula with first and second outlets. According to said method a gas flow is provided through the first outlet and a dynamic pressure signal in a gas path connected to the second outlet is measured. Optionally a parameter of the gas flow though the first outlet is adjusted in response to the measured signal.

Therein, the steps of providing a gas flow and measuring a dynamic pressure signal are preferably performed simultaneously. It is also preferred to perform the steps of the method repeatedly. According to a preferred embodiment, the functionality of the first and second outlets are interchanged after each repetition.

Thus, a flow of breathable gas is provided through, e.g., the first outlet of the nasal cannula to provide a certain flow rate or pressure within the respiratory tracts of a user. At the same time the second outlet and the gas path connected thereto are used to measure a dynamic pressure signal which originates from the respiratory tracts of the user. Since there is no fluid communication between the first and second outlets both steps can be preformed independently and simultaneously without any interference. It is therefore possible to provide therapy and to perform diagnostics at the same time.

Several different scenarios are envisaged for the embodiments of the present invention. One of them is background screening. A screening algorithm known in the art for treatment of OSA analyses the flow signal in the second flow path in order to detect or to diagnose apneas, hypopneas and flow limitations in the nasal flow. These events characterize the condition of the upper airway. The apneas and hypopneas go into an index calculation and the resulting index is displayed on a user interface of the device. It is thus possible to recognize a trend, e.g., in severity of the obstructive events. This is important for a transition from an open CPAP device as the one according to the present invention to a standard CPAP device that treats obstructive sleep apnea. The screening algorithm also comprises a snoring analysis, since permanent snoring is an indicator for a patient transition form an open device to a snoring or CPAP device.

It should be apparent that the function of the first and second outlets (and the flow paths connected thereto) may be interchanged repeatedly, e.g., after each respiratory cycle. Accordingly, the user is provided with the therapeutic air flow or pressure through both nostrils alternately. This guarantees a more symmetric and comfortable therapy.

Another scenario implemented by the present invention is an Auto Open CPAP Mode. Therein, the flow limitation algorithm part of the above-described screening algorithm delivers the data for a flow controlling algorithm. Thus, the parameters of the applied flow to the user's nose is depending on the number of flow limitations per time. According to the frequency of such events the flow rate or pressure of the applied gas flow may be adapted. Additionally or alternatively, the temperature and/or humidity of the applied breathing gas is adjusted.

A further scenario is a Smart Start/Stop Mode. According to a preferred embodiment both outlets of the nasal cannula and the respective flow paths are configured as diagnosis paths while the therapy is switched off and the device is on stand-by. A pressure change above a certain threshold, e.g. above +/−1 hPa, starts the therapy automatically. If during therapy no breathing signal is detected for a certain time, e.g. for more than 3 minutes, the device is switched to stand-by mode.

Alternatively to the Smart Start/Stop Mode there can be a nasal cannula alarm. The nasal cannula is likely to slip out of the user's nose/nostrils. The device may detect such an event, since no breathing signal is detected, an warn the user, e.g., by an alarm.

Still another scenario implemented by the present invention is an Open BiLevel Mode. In this mode, the device is triggered by the inspirational flow of a user, in particular by the flow rate provided at the beginning of an inspiration. The diagnosis channel detects this trigger event by comparing the nasal pressure or flow rate signal to a predetermined threshold. The threshold may be set to different sensitivities, e.g. high, medium and low. Once a trigger event is detected, a predetermined flow rate or pressure is provided to the selected therapy channel or corresponding flow path.

If the dynamic pressure signal at the diagnosis channel falls below a certain threshold, a flow with smaller flow rate (or pressure) is provided to the therapy channel or corresponding flow path. While the user is in expiration, the same amount of (humidified) air is provided to both outlets and thus to both nostrils of the user. During inspiration the diagnosis channel waits for the next trigger event.

It should be apparent that these scenarios described above can be implemented into the apparatus according to the present invention. Accordingly, the apparatus comprises a control unit adapted to analyze the detected signal(s) in the above-described manner and to control the respective components of the apparatus accordingly, e.g. to drive the blower unit and the valves.

The apparatus and the methods according to the present invention provide a number of advantages. In particular, the present invention allows, e.g., background screening, triggering and/or automatic controlling of an open CPAP device with a nasal cannula. The device is more comfortable for the patient and easier to use for both patient and physician. It allows a better adaptation to nasal conditions such as humidity. In a BiLevel mode no or only low flow during expiration can be achieved. Furthermore, the present invention allows permanent screening for sleep disordered breathing. A better compliance and the ability to observe a patient during, e.g., mild OSA, therapy is achieved.

These and other aspects of the invention will be apparent from and elucidated with reference to the embodiment(s) described hereinafter.

DETAILED DESCRIPTION OF EMBODIMENTS

Figure 1:
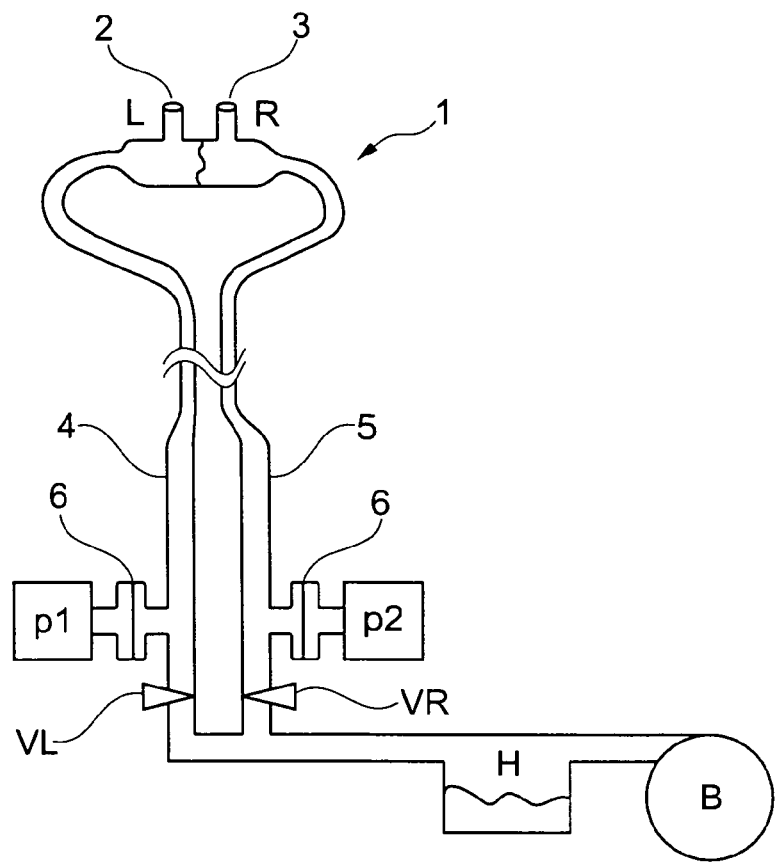
FIG. 1 schematically shows an embodiment of an apparatus according to the present invention.

FIG. 1 schematically shows an embodiment of an apparatus according to the present invention. Said apparatus comprises a blower unit B adapted to provide a flow of breathing gas, in particular of air. The blower unit comprises, e.g. a compressor (not shown in FIG. 1) known in the art and optionally means (not shown in FIG. 1) for adjusting, e.g., the concentration of oxygen or another additive. The flow of breathing gas is directed through an humidifier H, which is adapted to adjust the humidity and optionally the temperature of the gas flow.

The flow of breathing gas then branches into a first flow path 4 and a second flow path 5, which paths 4, 5 may be opened and closed by valves VL and VR, respectively. The first and second flow paths 4, 5 comprise pressure sensors p1 and p2, which are protected from condensing water by diaphragm filters 6.

Both flow paths 4 and 5 terminate in a nasal cannula 1 having first and second outlets 2 and 3. There is no fluid communication between outlets 2 and 3 which allows for controlling the flow rate and/or pressure of flow paths 4 and 5 independently. For example, valve VL may be open, whereas valve VR is closed. A flow of breathable gas is thus provided from the blower unit B through the first flow path 4 and the first outlet 2 into, e.g., the left nostril of a user. Due to the respiratory cycle of the user a dynamic pressure signal is generated within the second flow path 5, which is detected at pressure sensor p2.

After one respiratory cycle, the components may interchange their function: Valve VL is closed while valve VR is opened. Now, a therapy flow is provided through the second flow path 5 and the second outlet 3 into the right nostril of the user, whereas diagnosis is performed in the first flow path 4 using pressure sensor p1.

Figure 2:
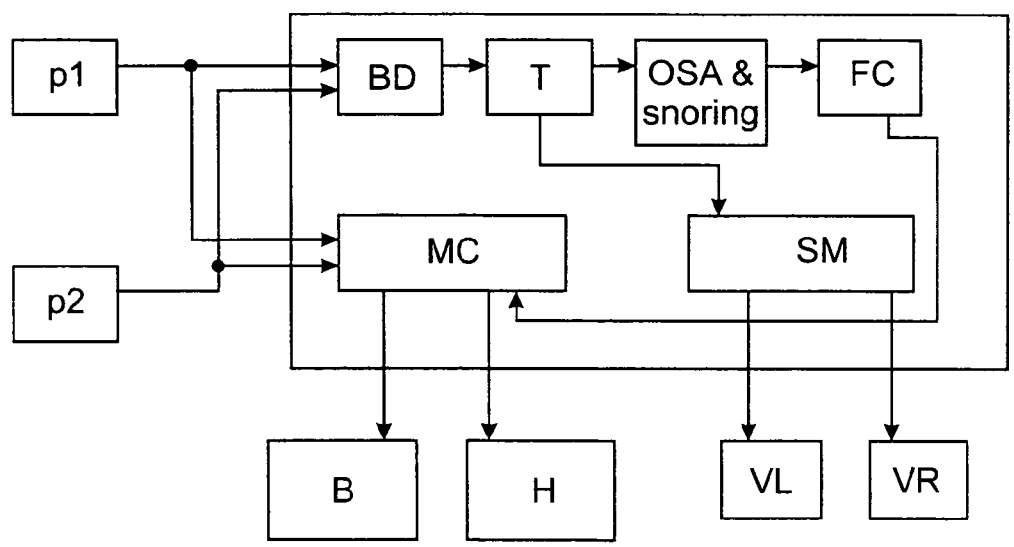
FIG. 2 schematically shows a circuit diagram of several components of the apparatus shown in FIG. 1.

FIG. 2 schematically shows a circuit diagram of several components of the apparatus shown in FIG. 1. The dynamic pressure signal detected at pressure sensors p1 and/or p2 is fed into a breathing detector BD and a motor controller MC. The breathing detector BD forwards the signal to a trigger module T, which outputs a trigger event to the flow controller FC and a supervisor module SM. The supervisor module SM controls the state of the valves VL and VR. The flow controller controls the motor controller MC, which activates the blower unit B and the humidifier H.

The invention claimed is:

1. An apparatus for controlled delivery of a flow of breathing gas to the respiratory tracts of a user, said apparatus comprising:
   a blower unit adapted to provide a gas flow; and
   a nasal cannula with first and second outlets, and first and second gas paths connecting the blower unit to the first and second outlets, respectively, wherein
   the nasal cannula is configured so that characteristics of the gas flow through each outlet are independently controllable, are independently adjustable and are independently sensed, and
   a control unit to control the apparatus to interchange between providing the gas flow to the respiratory tracts of the user through (a) the first gas path to the first outlet and (b) the second gas path to the second outlet, so as to permit providing of the gas flow from the blower unit through one of the outlets while not providing the gas flow from the blower unit through the other one of the outlets, and to adjust at least one characteristic of the provided gas flow while detecting, via one of the first or second outlets through its respective gas path not receiving the gas flow, at least one dynamic signal resulting from a respiratory cycle of the user.

2. The apparatus according to claim 1, wherein the characteristics of the gas flow comprise a flow rate and/or a pressure of the gas flow.

3. The apparatus according to claim 1, wherein the first and/or second gas path comprises a valve.

4. The apparatus according to claim 1, wherein the first and/or second gas path comprises a pressure sensor.

5. The apparatus according to claim 1, wherein functions of the first and second gas paths are interchanged periodically.

6. The apparatus according to claim 5, wherein the period of interchange is adjusted to the respiratory cycle of the user.

7. The apparatus according to claim 1, wherein the nasal cannula is adapted not to seal with the user's face and/or nostrils and/or wherein the apparatus is adapted to be used in an open CPAP system.

8. The apparatus according to claim 4, further comprising a humidifier positioned upstream of the first and second gas paths, the humidifier being configured to adjust a humidity and a temperature of the gas in the first and second gas paths.

9. The apparatus according to claim 8, wherein each pressure sensor is connected to a respective gas flow path through a filter configured to protect said pressure sensor from condensing water.

10. The apparatus according to claim 9, wherein the filter is a diaphragm filter.

11. The apparatus according to claim 1, wherein the apparatus is configured to detect a condition of an upper airway of the user based on the at least one dynamic signal, wherein the condition of the upper airway of the user is indicative of a flow limitation.

12. The apparatus according to claim 11, wherein the apparatus is configured to adjust at least one characteristic of the provided gas flow based on a number of flow limitations per unit of time.

13. The apparatus according to claim 12, wherein the at least one dynamic signal is a pressure signal.

14. The apparatus according to claim 1, wherein the apparatus is adapted to provide the gas flow to the respiratory tracts of the user through one of the first and second gas paths in response to a pressure change indicated by the at least one dynamic signal.

15. The apparatus according to claim 14, wherein the apparatus is adapted to provide the gas flow to the respiratory tracts of the user through one of the first and second gas paths when the pressure is above a predetermined threshold.

16. The apparatus according to claim 15, wherein the apparatus is adapted to terminate the gas flow to the respiratory tracts of the user when no dynamic signal is detected for a predetermined amount of time.

17. The apparatus according to claim 1, wherein the apparatus is adapted to provide the gas flow to the respiratory tracts of the user through one of the first and second gas paths in response to an inspirational flow indicated by the at least one dynamic signal.

18. The apparatus according to claim 17, wherein the at least one dynamic signal indicates the inspirational flow when the dynamic signal is above a first predetermined threshold.

19. The apparatus according to claim 18, wherein the first predetermined threshold is set to a high, medium or low sensitivity.

20. The apparatus according to claim 19, wherein the apparatus is adapted to reduce a flow rate of the gas flow provided to the respiratory tracts of the user when the at least one dynamic signal indicates an expirational flow.

21. The apparatus according to claim 20, wherein the at least one dynamic signal indicates the expirational flow when the dynamic signal is below a second predetermined threshold.

22. The apparatus according to claim 21, wherein the apparatus is adapted to provide the gas flow to the respiratory tracts of the user through both of the first and second gas paths while the user is in expiration.

23. The apparatus according to claim 1 wherein the control unit includes a screening process to detect flow limitation and a flow controlling process to respond to the detected flow limitation by adjusting applied gas flow rate to pneumatically splint an obstructed airway with at least one of the first or second outlets.

24. A method of controlling an apparatus for controlled delivery of a flow of breathing gas, wherein the apparatus comprises a blower unit adapted to provide a gas flow; and a nasal cannula with first and second outlets, and first and second gas paths connecting the blower unit to the first and second outlets, respectively, wherein the nasal cannula is configured so that characteristics of the gas flow through each outlet are independently controllable, are independently adjustable and are independently sensed, and a control unit to control the apparatus to interchange between providing the gas flow to the respiratory tracts of the user through (a) the first gas path to the first outlet and (b) the second gas path to the second outlet, so as to permit providing of the gas flow from the blower unit through one of the outlets while not providing the gas flow from the blower unit through the other one of the outlets, and to adjust at least one characteristic of the provided gas flow while detecting, via one of the first or second outlets through its respective gas path not receiving the gas flow, at least one dynamic signal resulting from a respiratory cycle of the user; said method comprising the following steps:
   a) providing a first gas flow in the first gas path;
   b) detecting a dynamic pressure signal in the second gas path; and
   c) adjusting a characteristic of the first gas flow in response to the detected dynamic pressure signal,
   wherein steps a) to c) are performed simultaneously.

25. The method according to claim 24, wherein steps a) to c) are performed repeatedly.

26. The method according to claim 25, wherein the function of the first and second gas paths are interchanged after each repetition.

27. The method of claim 24, wherein the apparatus is an open CPAP system.

28. A method of delivering a flow of breathable gas to the respiratory tracts of a user via a nasal cannula with first and second outlets, said method comprising the following steps:
   a) selectively providing the flow of breathable gas to the respiratory tracts of a user through the first outlet and the second outlet so as to interchangeably provide the flow through one of the outlets while not providing the flow through the other one of the outlets;
   b) measuring a dynamic pressure signal in a gas path connected to the one of the first and second outlets when not receiving the flow of breathable gas; and
   c) adjusting a parameter of the flow of breathable gas in response to the measured dynamic pressure signal,
   wherein steps a) to c) are performed simultaneously.

29. The method according to claim 28, wherein steps a) to c) are performed repeatedly.

30. The method according to claim 29, wherein functionalities of the first and second outlets are interchanged after each repetition.

31. The method according to claim 28, wherein the method further comprises humidifying and adjusting a temperature of the flow of breathable gas.

32. The method according to claim 28, further comprising:
  d) analyzing the dynamic pressure signal to detect flow limitations; and
  e) adjusting a parameter of the gas flow depending on frequency of detected flow limitations.

33. The method according to claim 32, wherein the parameter of the gas flow is one of: a flow rate of the gas flow, and a pressure of the gas flow.

34. The method according to claim 28 wherein a screening process detects flow limitation and a flow controlling process responds to the detected flow limitation by adjusting applied gas flow rate to pneumatically splint an obstructed airway with at least one of the first or second outlets.

* * * * *